(12) United States Patent
Takahashi et al.

(10) Patent No.: US 11,053,372 B2
(45) Date of Patent: Jul. 6, 2021

(54) CURING ACCELERATOR FOR OXIDATIVELY POLYMERIZED UNSATURATED RESIN, PRINTING INK, AND PAINT

(71) Applicant: DIC Corporation, Tokyo (JP)

(72) Inventors: Akinori Takahashi, Ichihara (JP); Takayuki Odashima, Ichihara (JP)

(73) Assignee: DIC Corporation, Tokyo (JP)

( * ) Notice: Subject to any disclaimer, the term of this patent is extended or adjusted under 35 U.S.C. 154(b) by 0 days.

(21) Appl. No.: 16/614,915

(22) PCT Filed: May 15, 2018

(86) PCT No.: PCT/JP2018/018686
§ 371 (c)(1),
(2) Date: Nov. 19, 2019

(87) PCT Pub. No.: WO2018/225465
PCT Pub. Date: Dec. 13, 2018

(65) Prior Publication Data
US 2020/0190284 A1     Jun. 18, 2020

(30) Foreign Application Priority Data

Jun. 8, 2017   (JP) .............................. JP2017-113406

(51) Int. Cl.
*C07D 213/46*     (2006.01)
*C07D 215/14*     (2006.01)
(Continued)

(52) U.S. Cl.
CPC .......... *C08K 5/3465* (2013.01); *C07D 213/46* (2013.01); *C07D 213/55* (2013.01);
(Continued)

(58) Field of Classification Search
None
See application file for complete search history.

(56) References Cited

U.S. PATENT DOCUMENTS 2,852,405 A    9/1958   Myers et al.
2,961,331 A    11/1960   Wheeler et al.
(Continued)

FOREIGN PATENT DOCUMENTS

EP         3636716 A1    4/2020
JP         S58-138765 A    8/1983
(Continued)

OTHER PUBLICATIONS

Allan, J. R. et al., "The Spectral and Magnetic Properties of Some Chloro and Bromo Transition Metal Complexes of Picolinic Acid and a Study of Their Performance as Colouring Materials for Poly(Vinyl Chloride)". European Polymer Journal 1986, 22(12), 973-977. (Year: 1986).*

(Continued)

*Primary Examiner* — Richard A Huhn
(74) *Attorney, Agent, or Firm* — Locke Lord LLP; James E. Armstrong, IV; Nicholas J. DiCeglie, Jr.

(57) ABSTRACT

Provided are a curing accelerator for an oxidative polymerization type unsaturated resin having a high curing accelerating ability, and a printing ink and a coating material. Specifically, there are provided a curing accelerator for an oxidative polymerization type unsaturated resin, containing a metal complex (β) having an anion compound (α) represented by the following structural formula (1-1) or (1-2) as a ligand:

(Continued)

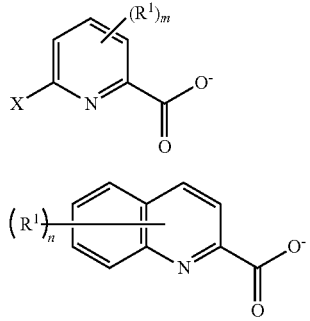

wherein R¹ is any one of a hydroxyl group, an amino group, a nitro group, a nitroso group, a sulfo group, a halogen atom, a hydrocarbon group which may have a substituent, a hydrocarbon oxy group which may have a substituent, and a hydrocarbon oxycarbonyl group which may have a substituent, m is 0 or an integer of 1 to 3, n is 0 or an integer of 1 to 6, and X is any one of a carboxylate group, a hydrogen atom, and the R¹ group.

10 Claims, 1 Drawing Sheet

(51) Int. Cl.
    *C08K 5/3465*      (2006.01)
    *C09D 7/63*        (2018.01)
    *C09D 11/03*       (2014.01)
    *C09D 201/00*      (2006.01)
    *C07D 213/55*      (2006.01)
(52) U.S. Cl.
    CPC ............ *C07D 215/14* (2013.01); *C09D 7/63* (2018.01); *C09D 11/03* (2013.01); *C09D 201/00* (2013.01)

(56) References Cited

U.S. PATENT DOCUMENTS

| | | |
|---|---|---|
| 5,439,863 A | 8/1995 | Bottcher et al. |
| 2004/0024140 A1 | 2/2004 | Fujita et al. |
| 2018/0237645 A1 | 8/2018 | Tsutsumi et al. |

FOREIGN PATENT DOCUMENTS

| | | |
|---|---|---|
| JP | 60-108461 A | 6/1985 |
| JP | S60108461 A | 6/1985 |
| JP | 06-172689 A | 6/1994 |
| JP | 2000-191711 A | 7/2000 |
| JP | 2007-107010 A | 4/2007 |
| JP | 2015151468 A | 8/2015 |
| JP | 5933733 B2 | 6/2016 |
| WO | 2015005121 A1 | 1/2015 |
| WO | 2017/043406 A1 | 3/2017 |

OTHER PUBLICATIONS

International Search Report dated Aug. 21, 2018, issued for PCT/JP2018/018686.

Extended European Search Report issued in EP 18813764.0, dated Feb. 5, 2021.

Wang et al. "New Ligands for the Fe(III)-Mediated Reverse Atom Transfer Radical Polymerization of Methyl Methacrylate", Journal of Polymer Science, Part A: Polymer Chemistry, vol. 44, 2912-2921, (2006).

Dobrzynska et al., "Crystal Structure and Characterization of Manganese(II) Carboxylates: 3D Metal-Organic Frameworks", Crystal Growth & Design, vol. 5, No. 5, 1945-1951 (2005).

Devereux et al., "Synthesis and catalytic activity of manganese(II) complexes of heterocyclic carboxylic acids: X-ray crystal structures of [Mn(pyr)2]n, [Mn(dipic)(bipy)2].4.5H2O and [Mn(chedam)(bipy)].H2O (pyr = 2-pyrazinecarboxylic acid; dipic = pyridine-2,6-dicarboxylic acid; chedam = chelidamic acid(4-hydroxypyridine-2,6-dicarboxylic acid); bipy = 2,2-bipyridine)", Polyhedron 21, 1063-1071, (2002).

* cited by examiner

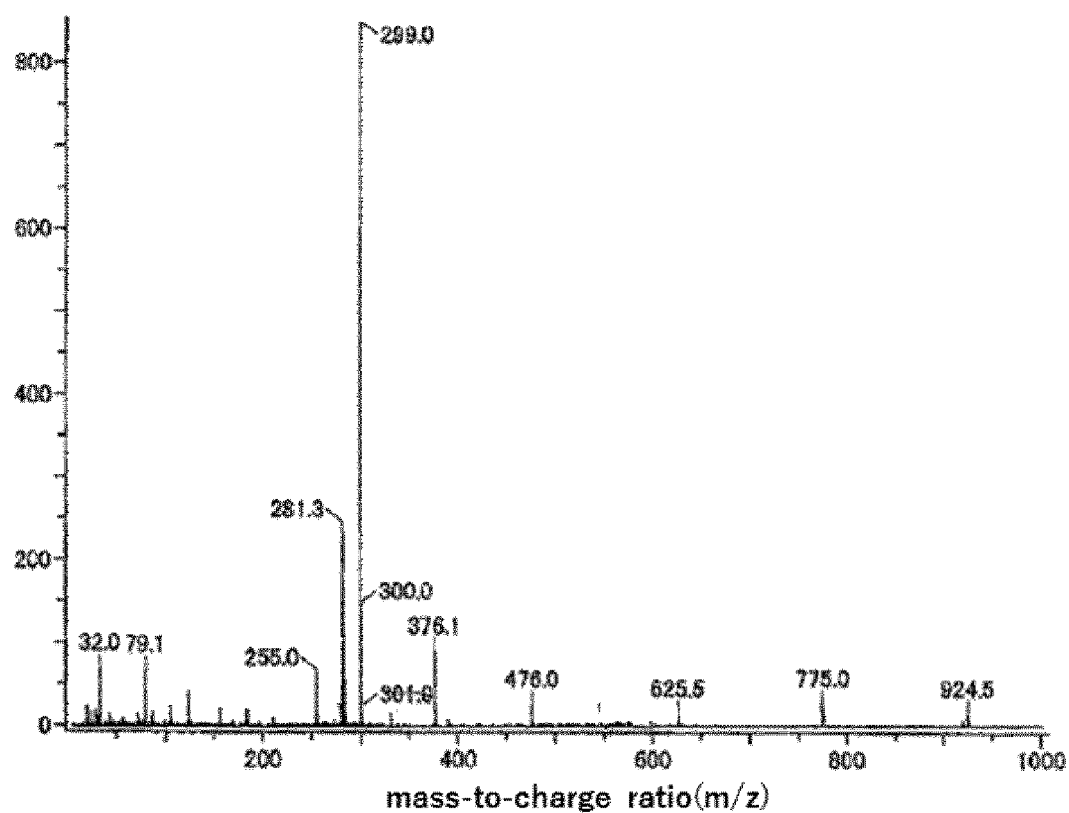

CURING ACCELERATOR FOR OXIDATIVELY POLYMERIZED UNSATURATED RESIN, PRINTING INK, AND PAINT

TECHNICAL FIELD

The present invention relates to a curing accelerator for an oxidative polymerization type unsaturated resin having a high curing accelerating ability, and to a printing ink and a coating material each including the curing accelerator.

BACKGROUND ART

In a field using an oxidative polymerization type resin as a structural component, such as a printing ink and a coating material, a drier is added as a curing accelerator for drying the resin. As the drier used in the ink or the coating material, a metal salt of a heavy metal such as cobalt, manganese, lead, iron, or zinc and various carboxylic acids (hereinafter, may be abbreviated as "metal soap") is generally used.

Particularly, a cobalt metal soap has excellent drying performance, however, in a case where a large amount thereof is used for obtaining higher drying performance, surface drying of an ink or a coating film may extremely rapidly proceed, and thus, the cobalt metal soap may be a reason of wrinkles or shrinkage. Therefore, as a method of obtaining high drying performance while preventing such wrinkles or shrinkage, a curing accelerator containing both of a cobalt metal soap and bipyridyl has been proposed (for example, see PTL 1). This curing accelerator prevented wrinkles or shrinkage and had high drying performance.

However, cobalt compounds are listed up in Group 2B of "Possibly carcinogenic to humans" in the carcinogenicity risk list by the International Agency for Research on Cancer, and accordingly, carcinogenicity of the cobalt compounds is concerned. In addition, metal cobalt is a rare metal and supplying thereof is unstable, and accordingly, the price of the cobalt metal soap is high. Therefore, a curing accelerator having high drying performance in which no cobalt soap is used or a decreased amount of the cobalt metal soap is used is required.

CITATION LIST

Patent Literature

PTL 1: JP-A-06-172689

SUMMARY OF INVENTION

Technical Problem

A problem to be solved the present invention is to provide a curing accelerator for an oxidative polymerization type unsaturated resin having curing performance equal to or higher than excellent curing performance of cobalt metal soap, having high solubility in organic solvents, being usable outdoors, and having excellent versatility, without using the cobalt metal soap which may affect a human body, or by using a small amount thereof compared to that in the related art, and a printing ink and a coating material using the same.

Solution to Problem

As a result of intensive studies, the present inventors have found that the above problems can be solved by a metal complex including an anionic compound having a picolinic acid skeleton as a ligand, and thus the present invention has been completed.

That is, the present invention provides a curing accelerator for an oxidative polymerization type unsaturated resin, which includes a metal complex (β) having an anion compound (α) represented by the following structural formula (1-1) or (1-2) as a ligand:

[Chem. 1]

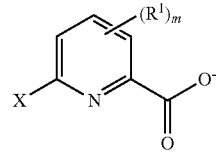

(1-1)

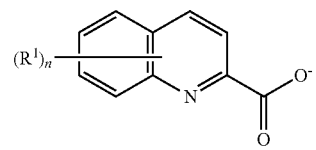

(1-2)

In the formula, $R^1$ is any one of a hydroxyl group, an amino group, a nitro group, a nitroso group, a sulfo group, a halogen atom, a hydrocarbon group which may have a substituent, a hydrocarbon oxy group which may have a substituent, and a hydrocarbon oxycarbonyl group which may have a substituent, m is 0 or an integer of 1 to 3, n is 0 or an integer of 1 to 6, and X is any one of a carboxylate group, a hydrogen atom, and a $R^1$ group.

The present invention also provides a curing accelerator for an oxidative polymerization type unsaturated resin, which includes a compound (A) represented by the following structural formula (2-1) or (2-2):

[Chem. 2]

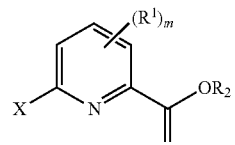

(2-1)

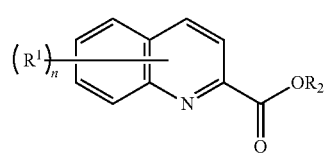

(2-2)

In the formula, $R^1$ is any one of a hydroxyl group, an amino group, a nitro group, a nitroso group, a sulfo group, a halogen atom, a hydrocarbon group which may have a substituent, a hydrocarbon oxy group which may have a substituent, and a hydrocarbon oxycarbonyl group which may have a substituent, m is 0 or an integer of 1 to 3, n is 0 or an integer of 1 to 6, $R^2$ is a hydrogen atom or an aliphatic hydrocarbon group, and X is any one of —$COOR^2$ group, a hydrogen atom, and the $R^1$ group, and a metal salt (B).

Further, the present invention provides a printing ink and a coating material including the curing accelerator for an oxidative polymerization type unsaturated resin and an oxidative polymerization type unsaturated resin.

Advantageous Effects of Invention

The curing accelerator for an oxidative polymerization type unsaturated resin of the present invention solves the problems of carcinogenic properties of metal cobalt, supply instability and cost of raw materials, and has a short curing time and excellent curing performance. Further, it is excellent in solubility in a general-purpose organic solvent, can be used outdoors, and can be suitably used as a curing accelerator for an oxidative polymerization dry type printing ink or coating material represented by a lithographic printing ink.

BRIEF DESCRIPTION OF DRAWINGS

FIG. 1 is an MS spectrum of the product of Preparation Example 1.

DESCRIPTION OF EMBODIMENTS

A curing accelerator for an oxidative polymerization type unsaturated resin of the present invention includes a metal complex (β) having an anion compound (α) represented by the following structural formula (1-1) or (1-2) as a ligand:

[Chem. 3]

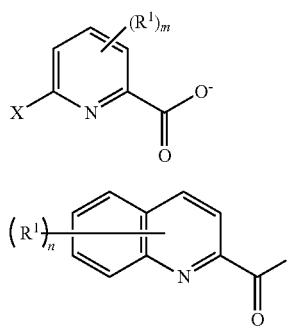

(1-1)

(1-2)

In the formula, $R^1$ is any one of a hydroxyl group, an amino group, a nitro group, a nitroso group, a sulfo group, a halogen atom, a hydrocarbon group which may have a substituent, a hydrocarbon oxy group which may have a substituent, and a hydrocarbon oxycarbonyl group which may have a substituent, m is 0 or an integer of 1 to 3, n is 0 or an integer of 1 to 6, and X is any one of a carboxylate group, a hydrogen atom, and the $R^1$ group.

In the present invention, a metal complex (β) synthesized in advance may be used, or a compound (A) represented by the following structural formula (2-1) or (2-2) and a metal salt (B) may be mixed to generate a metal complex (β):

[Chem. 4]

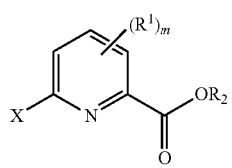

(2-1)

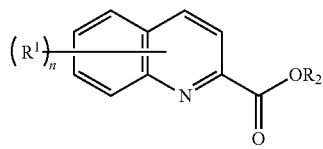

(2-2)

In the formula, $R^1$ is any one of a hydroxyl group, an amino group, a nitro group, a nitroso group, a sulfo group, a halogen atom, a hydrocarbon group which may have a substituent, a hydrocarbon oxy group which may have a substituent, and a hydrocarbon oxycarbonyl group which may have a substituent, m is 0 or an integer of 1 to 3, n is 0 or an integer of 1 to 6, $R^2$ is a hydrogen atom or an aliphatic hydrocarbon group, and X is any one of —$COOR^2$ group, a hydrogen atom, and the $R^1$ group.

$R^1$ in the structural formulas (1-1), (1-2) and (2-1), (2-2) is any one of a hydroxyl group, an amino group, a nitro group, a nitroso group, a sulfo group, a halogen atom, a hydrocarbon group which may have a substituent, a hydrocarbon oxy group which may have a substituent, and a hydrocarbon oxycarbonyl group which may have a substituent. The halogen atom may be any one of fluorine, chlorine, bromine, and iodine. The hydrocarbon group in the hydrocarbon group, the hydrocarbon oxy group, and the hydrocarbon oxycarbonyl group may be any one of an aliphatic hydrocarbon group, an alicyclic structure-containing hydrocarbon group, and an aromatic ring-containing hydrocarbon group. The aliphatic hydrocarbon group may have a straight chain or branched structure, and may have an unsaturated group in its structure. Examples of the substituents on the hydrocarbon group, the hydrocarbon oxy group, or the hydrocarbon oxycarbonyl group include a hydroxyl group, an amino group, a nitro group, a nitroso group, a sulfo group, a halogen atom, an alkyl group, and an alkoxy group.

In the structural formula (2-1), X is any one of a carboxyl group, a hydrogen atom, and a $R^1$ group. Among them, a carboxyl group or a hydrogen atom is preferable because it is excellent in its performance as a curing accelerator. In the same manner, X in the structural formula (1-1) is preferably a carboxylate group or a hydrogen atom.

$R^2$ in the structural formulas (2-1) and (2-2) is a hydrogen atom or an aliphatic hydrocarbon group. The number of carbon atoms of the aliphatic hydrocarbon group is not particularly limited, and it may be either a relatively short chain having 1 to 6 carbon atoms or a relatively long chain having 7 or more carbon atoms. The aliphatic hydrocarbon group may have a straight chain or branched structure, and may have an unsaturated group in its structure. Among these, $R^2$ is preferably a hydrogen atom or an alkyl group having 1 to 4 carbon atoms, because the ligand exchange with the metal salt (B) is easily generated.

The metal salt (B) is not particularly limited as long as it is capable of undergoing ligand exchange in the presence of the compound (A) to form a metal complex (β) having the anion compound (α) as a ligand, and examples thereof include those represented by the following general formula (B-1):

[Chem. 5]

$$M(X)_n \quad (B\text{-}1)$$

In the formula, the central metal expressed by M is any one of manganese, iron, cobalt, bismuth, zirconium, barium, calcium, strontium, nickel, copper, zinc, cerium, and vanadium; X is any one of $F^-$, $Cl^-$, $Br^-$, $I^-$, $PF_6^-$, $SbF_6^-$, $AsF_6^-$, $BF_4^-$, $B(C_6F_5)_4^-$, $ClO_4^-$, $ClO_3^-$, $CO_2^-$, $ClO^-$, $H_2PO_4^-$, $H_2PO_3^-$, $H_2PO_2^-$, $HCO_3^-$, $NO_3^-$, $NO_2^-$, $(CH_3CO)_2CH^-$, $RCOO^-$ (wherein R is a hydrocarbon group having 1 to 22 carbon atoms), $O^{2-}$, $S^{2-}$, $SO_4^{2-}$, $SO_3^{2-}$, and $CO_3^{2-}$; and n is an integer of 1 or more. These may be used alone or in combination of two or more kinds thereof.

Among these, it is preferable that the central metal of the metal salt (B), that is, the central metal of the metal complex (β) is manganese or iron because of its excellent performance as a curing accelerator. The valence of the central metal of the metal complex (β) is not particularly limited, and in a case where the central metal is manganese, for example, it usually has a valence of 2 to 7. When the central metal is iron, it is usually a divalent or trivalent complex. Further, since the metal salt (B) has excellent solubility in printing ink or coating material, it is preferable that the metal salt (B) is a fatty acid salt of the general formula (B-1) in which X is a $RCOO^-$ (wherein R is a hydrocarbon group having 1 to 22 carbon atoms), and it is particularly preferable that the metal salt (B) is an octylate, a neodecanate, an isononanate, or a naphthenate.

For the mixing ratio of the compound (A) and the metal salt (B), the ratio of the compound (A) to 1 mol of the metal atom in the metal salt (B) is preferably in a range of 0.1 to 20 mol, more preferably in a range of 0.2 to 10 mol, and particularly preferably in a range of 0.5 to 5 mol, so that the curing accelerator can have excellent performance.

The mixing of the compound (A) and the metal salt (B) is preferably carried out in a solvent capable of dissolving both of them. The solvent is not particularly limited, and examples thereof include a variety of organic solvents widely used in printing inks and coating applications. When an imidazole compound (C) or a benzyl alcohol compound (D) to be described later is capable of dissolving the compound (A) and the metal salt (B), the imidazole compound (C) or the benzyl alcohol compound (D) may be used as a solvent. Examples of the various organic solvents include hydrocarbon solvents such as toluene, xylene, heptane, hexane, and mineral spirit; alcohol solvents such as methanol, ethanol, propanol, and cyclohexanol; ketone solvents such as methyl ethyl ketone, methyl isobutyl ketone, and cyclohexanone; ether solvents such as propyl ether, methyl cellosolve, cellosolve, butyl cellosolve, and methyl carbitol; vegetable oils and fats such as soybean oil, linseed oil, rapeseed oil, and safflower oil; fatty acid esters represented by R—COOR' (wherein R is an alkyl group having 5 to 11 carbon atoms and R' is an alkyl group having 1 to 3 carbon atoms); "Spindle Oil No. 1", "Solvent No. 3", "Solvent No. 4", "Solvent No. 5", "Solvent No. 6", "Naphtesol H", and "Alkene 56NT" manufactured by JXTG Nippon Oil & Energy Corporation; "Diadol 13" and "Dialen 168" manufactured by Mitsubishi Chemical Corporation; "F OXO-COL" and "F OXOCOL 180" manufactured by NISSAN CHEMICAL INDUSTRIES, Ltd.; "AF Solvent No. 4", "AF Solvent No. 5", "AF Solvent No. 6", And "AF Solvent No. 7" manufactured by JXTG Nippon Oil & Energy Corporation; D-SOL solvent "Solvent H" manufactured by ISU EXACHEM Co., Ltd.; "N-Paraffin C14-C18" manufactured by ISU EXACHEM Co., Ltd.; "Supersol LA35" and "Supersol LA38" manufactured by Idemitsu Kosan Co., Ltd.; "Exxsol D80", "Exxsol D110", "Exxsol D120", "Exxsol D130", "Exxsol D160", "Exxsol D100K", "Exxsol D120K", "Exxsol D130K", "Exxsol D280", "Exxsol D300", and "Exxsol D320" manufactured by EXXON Chemical Co., Ltd.; and "Magiesol 40", "Magiesol 44", "Magiesol 47", "Magiesol 52", and "Magiesol 60" manufactured by Magie Brothers Oil Company. These diluents may be used alone or in combination of two or more kinds thereof.

When the curing accelerator for an oxidative polymerization type unsaturated resin of the present invention is prepared, the compound (A) and other ligands (A') other than the compound (A) may be used in combination. Examples of the other ligand (A') include amino alcohol compounds, 2,2'-bipyridyl and derivatives thereof, 1,10-phenanthroline and derivatives thereof, N,N'-bissalicylidene 1,2-propanediamine and derivatives thereof, 8-quinolinol and derivatives thereof. Examples of the derivative of a compound include a compound having one or more substituents such as a hydroxyl group, an amino group, a nitro group, a nitroso group, a sulfo group, a halogen atom, a hydrocarbon group which may have a substituent, a hydrocarbon oxy group which may have a substituent, and a hydrocarbon oxycarbonyl group which may have a substituent on an aromatic nucleus of the compound, and an alkyl ester of a carboxylic acid. For the above-mentioned various substituents, examples of the halogen atom include fluorine, chlorine, bromine, and iodine.

The hydrocarbon group in the hydrocarbon group, the hydrocarbon oxy group, and the hydrocarbon oxycarbonyl group may be any one of an aliphatic hydrocarbon group, an alicyclic structure-containing hydrocarbon group, and an aromatic ring-containing hydrocarbon group. The aliphatic hydrocarbon group may have a straight chain or branched structure, and may have an unsaturated group in its structure. Examples of the substituents on the hydrocarbon group, the hydrocarbon oxy group and the hydrocarbon oxycarbonyl group include a hydroxyl group, an amino group, a nitro group, a nitroso group, a sulfo group, a halogen atom, an alkyl group, and an alkoxy group.

These other ligands (A') may be used alone or in combination of two or more kinds thereof. When these other ligands (A') are used, the compound (A) is preferably used in a proportion of 50% by mol or more, and more preferably in a proportion of 80% by mol or more, based on the total of the compound (A) and the other ligand (A')

The curing accelerator for an oxidative polymerization type unsaturated resin of the present invention may contain other metal complexes (β'1) or metal soaps (β'2) other than the metal complex (β).

The other metal complex (β'1) is not particularly limited as long as it is a metal complex having a ligand (A') other than the compound (A), and any metal complex may be used. The central metal of the other metal complex (β') may be manganese, iron, cobalt, bismuth, zirconium, barium, calcium, strontium, nickel, copper, zinc, cerium, or vanadium as similar to the metal complex (β) of the present invention. These may be used alone or in combination of two or more kinds thereof. Among them, a metal salt of any one of bismuth, zirconium, barium, calcium, and strontium is preferable for excellent performance of the curing accelerator.

Examples of the metal soap (β'2) include metallic fatty acid salts in which X in the general formula (B-1) is RCOO— (wherein R is a hydrocarbon group having 1 to 22 carbon atoms) These may be used alone or in combination of two or more kinds thereof. Among them, a metal salt of any one of bismuth, zirconium, barium, calcium, and strontium is preferable because it is excellent in its performance as a curing accelerator.

When the other metal complex (β'1) or metal soap (β'2) in which the central metal is one or more than one kind of bismuth, zirconium or barium is used, it is preferable to use them in such a ratio that the amount of metal in the other metal complex (β'1) or metal soap (β'2) is 1 to 100 parts by mass and more preferably 3 to 40 parts by mass with respect to 1 part by mass of the metal in the metal complex (β).

When a metal salt of calcium or strontium is used as the other metal complex (β'1) or metal soap (β'2), it is preferable to use them in such a ratio that the amount of metal in the other metal complex (β'1) or metal soap (β'2) is 1 to 100 parts by mass with respect to 1 part by mass of the metal in the metal complex (β).

The curing accelerator for an oxidative polymerization type unsaturated resin of the present invention may further contain at least one of an imidazole compound (C) and a benzyl alcohol compound (D), thereby becoming a curing accelerator having a further excellent curing accelerating ability. Examples of the imidazole compound (C) include compounds represented by the following structural formula (C-1). Further, examples of the benzyl alcohol compound (D) include compounds represented by the following structural formula (D-1).

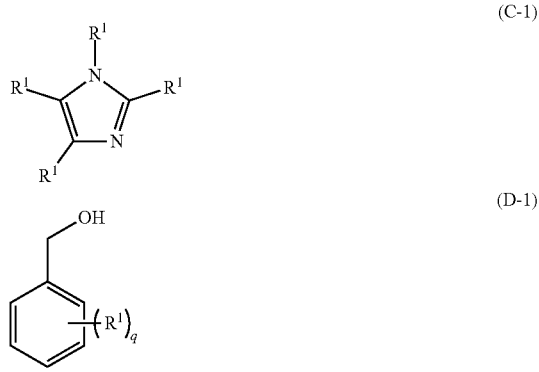

In the formulas, $R^1$ is independently any one of hydrogen, a hydroxyl group, an amino group, a nitro group, a nitroso group, a sulfo group, a halogen atom, a hydrocarbon group which may have a substituent, a hydrocarbon oxy group which may have a substituent, and a hydrocarbon oxycarbonyl group which may have a substituent, and q is 0 or an integer of 1 to 5.

The amount of the imidazole compound (C) added is preferably in a range of 10 to 500 parts by mass with respect to 10 parts by mass of the metal complex (β). Alternatively, the amount of the imidazole compound (C) added is preferably in a range of 5 to 200 parts by mass with respect to 10 parts by mass of the total of the compound (A) and the metal salt (B). The amount of the benzyl alcohol compound (D) added is preferably in a range of 10 to 500 parts by mass with respect to 10 parts by mass of the metal complex (β). Alternatively, the amount of the benzyl alcohol compound (D) added is preferably in a range of 5 to 200 parts by mass with respect to 10 parts by mass of the total of the compound (A) and the metal salt (B).

A curable resin composition of the present invention includes the above-mentioned curing accelerator for an oxidative polymerization type unsaturated resin and an oxidative polymerization type unsaturated resin as essential components, and may contain an organic solvent, various additives, and the like. The oxidative polymerization type unsaturated resin used here may be of any type that has an unsaturated bond in the molecular structure and allows the unsaturated bond to undergo oxidative polymerization with oxygen in the air. Specifically, in a case of being used for the printing ink, a rosin-modified phenolic resin, an unsaturated group-containing polyester resin, an alkyd resin, a petroleum resin, polymerized oil, and the like are used. In addition, in a case of being used for the coating material, an alkyd resin, an unsaturated group-containing urethane resin, an unsaturated group-containing epoxy resin, an unsaturated group-containing polyester resin, polymerized oil, and the like are used. These oxidative polymerization type unsaturated resins may be used alone or in combination of two or more kinds thereof.

The method for producing the curable resin composition of the present invention is not particularly limited and may be produced by any method. Examples include a method in which a curing accelerator for an oxidative polymerization type unsaturated resin is obtained by previously synthesizing the metal complex (β), or is prepared by mixing the compound (A) and the metal salt (B) in advance, which is then mixed with an oxidative polymerization type unsaturated resin and other components; a method in which one of the compound (A) and the metal salt (B) is previously mixed with an oxidative polymerization type unsaturated resin and other components, and the other one of the compound (A) and the metal salt (B) is added thereto; and a method in which the compound (A), the metal salt (B), the oxidative polymerization type unsaturated resin, and the other components are mixed together.

Further, in a case where the other metal complex (β'1) or metal soap (β'2) described as an optional component of the curing accelerator for an oxidative polymerization type unsaturated resin is used, examples of the addition method include, for example, a method in which these components are added to a curing accelerator for an oxidative polymerization type unsaturated resin which is obtained by previously synthesizing the metal complex (β) or a curing accelerator for an oxidative polymerization type unsaturated resin which is obtained by previously mixing the compound (A) and the metal salt (B); a method in which these components are added when a curing accelerator for an oxidative polymerization type unsaturated resin is mixed with an oxidative polymerization type unsaturated resin; and a method in which these components are mixed together in combination with the compound (A), the metal salt (B), and the oxidative polymerization type unsaturated resin.

A case of using the curing accelerator for an oxidative polymerization type unsaturated resin of the present invention for the printing ink will be described. The printing ink includes a pigment or a dye, a gelling agent, a surface modifier, a drying inhibitor, vegetable oil, various organic solvents, and the like, in addition to the curing accelerator for an oxidative polymerization type unsaturated resin and the oxidative polymerization type unsaturated resin. A mixing ratio of each component or the kind of mixtures is suitably adjusted depending on a printing system. The curing accelerator for an oxidative polymerization type unsaturated resin of the present invention can also be suitably used in a printing ink of any system such as a lithographic offset ink, a waterless lithographic ink, and a letterpress ink.

The amount of the curing accelerator for an oxidative polymerization type unsaturated resin mixed in the printing ink is preferably in a range of 0.001 to 5 parts by mass in 100 parts by mass of the printing ink, from viewpoints of realizing an ink which has a short drying time and skinning of which hardly occurs.

For the pigment, organic pigments for a printing ink disclosed in "Organic Pigment Handbook (writer: Isao Hashimoto, Publisher: Color Office, 2006, the first edition)" is used, for example, and a soluble azo pigment, an insoluble azo pigment, a condensed azo pigment, a metal phthalocyanine pigment, a metal-free phthalocyanine pigment, a quinacridone pigment, a perylene pigment, perinone pigment, an isoindolinone pigment, an isoindoline pigment, a dioxazine pigment, a thioindigo pigment, an anthraquinone-based pigment, a quinophthalone pigment, a metal complex pigment, a diketopyrrolopyrrole pigment, a carbon black pigment, and other polycyclic pigments can be used. In the present invention, inorganic pigments can also be used, and for example, inorganic extender pigments such as carbonate lime powder, precipitated calcium carbonate, gypsum, clay (China Clay), silica powder, diatomaceous earth, talc, kaolin, alumina white, barium sulfate, aluminum stearate, magnesium carbonate, baryte powder, and polishing powder, silicone, or glass beads are used, in addition to inorganic colored pigments such as titanium oxide, graphite, and zinc flower. The amount of these pigments mixed depends on the kinds of the desired printing ink, and is normally preferably in a range of 5 to 55 parts by mass in 100 parts by mass of the printing ink.

The gelling agent is used for adjusting viscoelasticity for the printing ink, and examples thereof include an organo-aluminum compound, an organic titanate compound, an organozinc compound, and an organo-calcium compound. The gelling agents may be used alone or in combination of two or more kinds thereof. Among these, the organoaluminum compound is preferable, and examples of the organo-aluminum compound include aluminum alcoholate and aluminum chelate compounds. In addition, examples of the aluminum chelate compound include aluminum diisopropoxide monoethyl acetoacetate, aluminum di-n-butoxide monomethyl acetoacetate, aluminum di-n-butoxide monoethyl acetoacetate, aluminum di-i-butoxide monomethyl acetoacetate, aluminum di-sec-butoxide monoethyl acetoacetate, aluminum tris(acetylacetonate), aluminum tris(ethyl acetoacetonate), and aluminum mono-acetylacetonate bis (ethyl acetoacetonate). The amount of the gelling agent added depends on the kinds of the desired printing ink, and is normally in a range of 0.1 to 5 parts by mass in 100 parts by mass of the printing ink.

The surface modifier is added in order to improve abrasion resistance, blocking preventing properties, sliding properties, scratch preventing properties, and other properties of an ink coating film, and examples thereof include natural wax such as carnauba wax, wood wax, lanolin, montan wax, paraffin wax, or microcrystalline wax; and synthesis wax such as Fischer-Tropsch wax, polyethylene wax, polypropylene wax, polytetrafluoroethylene wax, polyamide wax, or a silicone compound. The amount of the surface modifier mixed depends on the kinds of the desired printing ink, and is normally preferably in a range of 0.1 to 7.0 parts by mass in 100 parts by mass of the printing ink.

The drying inhibitor is added in order to improve storage stability of the printing ink and prevent skinning, and examples thereof include hydroquinone, methoquinone, and tert-butyl hydroquinone. The amount of the drying inhibitor mixed depends on the kinds of the desired printing ink, and is normally in a range of 0.01 to 5 parts by mass in 100 parts by mass of the printing ink.

Examples of the vegetable oil include monoester of the vegetable oil fatty acid such as linseed oil fatty acid methyl ester, soybean oil fatty acid methyl ester, linseed oil fatty acid ethyl ester, soybean oil fatty acid ethyl ester, linseed oil fatty acid propyl ester, soybean oil fatty acid propyl ester, linseed oil fatty acid butyl ester, or soybean oil fatty acid butyl ester, in addition to vegetable oil such as linseed oil, tung oil, rice oil, safflower oil, soybean oil, tall oil, rapeseed oil, palm oil, castor oil, or coconut oil and fat, and recycled vegetable oil obtained by being subjected to a recycling treatment after using these vegetable oils for food processing. These may be used alone or in combination of two or more kinds thereof. Among these, the vegetable oil including an unsaturated bond in a molecule such as linseed oil, tung oil, or soybean oil is preferable, from a viewpoint of producing a printing ink having excellent drying properties, and soybean oil or recycled oil thereof is more preferable, from a viewpoint of small environmental loads.

Examples of the organic solvent include "Spindle Oil No. 1", "Solvent No. 3", "Solvent No. 4", "Solvent No. 5", "Solvent No. 6", "Naphtesol H", and "Alkene 56NT" manufactured by JXTG Nippon Oil & Energy Corporation; "Diadol 13" and "Dialen 168" manufactured by Mitsubishi Chemical Corporation; "F OXOCOL" and "F OXOCOL 180" manufactured by NISSAN CHEMICAL INDUSTRIES, Ltd.; "AF Solvent No. 4", "AF Solvent No. 5", "AF Solvent No. 6", And "AF Solvent No. 7" manufactured by JXTG Nippon Oil & Energy Corporation; D-SOL solvent "Solvent H" manufactured by ISU EXACHEM Co., Ltd.; "N-Paraffin C14-C18" manufactured by ISU EXACHEM Co., Ltd.; "Supersol LA35" and "Supersol LA38" manufactured by Idemitsu Kosan Co., Ltd.; "Exxsol D80", "Exxsol D110", "Exxsol D120", "Exxsol D130", "Exxsol D160", "Exxsol D100K", "Exxsol D120K", "Exxsol D130K", "Exxsol D280", "Exxsol D300", and "Exxsol D320" manufactured by EXXON Chemical Co., Ltd.; and "Magiesol 40", "Magiesol 44", "Magiesol 47", "Magiesol 52", and "Magiesol 60" manufactured by Magie Brothers Oil Company.

The amount of the vegetable oil or the organic solvent added depends on the kinds of the desired printing ink, and is normally in a range of 20 to 80 parts by mass in 100 parts by mass of the printing ink.

As a method of preparing the printing ink, for example, a method of milling a mixture of the oxidative polymerization type unsaturated resin, the pigment, the vegetable oil, the organic solvent, and various additives by an ink mill such as three-roll ink mill is used. The curing accelerator for an oxidative polymerization type unsaturated resin of the present invention may be added at the time of the milling or may be added after the milling. Further, as the method for adding the curing accelerator for an oxidative polymerization type unsaturated resin, it may be added as a curing accelerator for an oxidative polymerization type unsaturated resin obtained by mixing the compound (A) and the metal salt (B) in advance as described above, or the compound (A) and the metal salt (B) may be separately mixed. When a rosin-modified phenolic resin having high versatility is used as an oxidative polymerization type unsaturated resin, the rosin-modified phenolic resin and a vegetable oil, an organic solvent, a gelling agent, and the like may be preliminarily mixed to form a varnish, and a mixture of the resulting varnish and a pigment, a vegetable oil, an organic solvent, various additives and the like may be subjected to milling using a mill such as a three-roll mill.

A case of using the curing accelerator for an oxidative polymerization type unsaturated resin of the present invention for the coating material will be described. The coating material includes a pigment, a pigment dispersing agent, a drying inhibitor, a surface modifier, an ultraviolet absorber, a defoaming agent, a thickener, an anti-settling agent, vegetable oil, or various organic solvents, in addition to the curing accelerator for an oxidative polymerization type unsaturated resin and the oxidative polymerization type unsaturated resin. A mixing ratio of each component or the kinds of mixtures is suitably adjusted depending on the purpose or the desired performance of the coating material.

The amount of the curing accelerator for an oxidative polymerization type unsaturated resin mixed in the coating material is preferably in a range of 0.001 to 5 parts by mass in 100 parts by mass of the coating material, from viewpoints of realizing a coating material which has a short drying time and of which skinning hardly occurs.

As described above, examples of the oxidative polymerization type unsaturated resin used for the coating material include an alkyd resin, an unsaturated group-containing urethane resin, and an unsaturated group-containing epoxy resin. The alkyd resin having particularly high versatility among these is a kind of polyester resin in which a polybasic acid compound, a polyhydric alcohol compound, and an oil fatty acid are main raw material components.

As the polybasic acid compound, for example, dibasic acids such as phthalic anhydride, isophthalic acid, terephthalic acid, tetrahydrophthalic anhydride, hexahydrophthalic anhydride, succinic acid, fumaric acid, adipic acid, sebacic acid, and maleic anhydride; and lower alkyl esterified material of these acids are mainly used. In addition, tri- or higher valent polybasic acids such as trimellitic anhydride, methylcyclohexene tricarboxylic acid, or pyromellitic anhydride; sulfophthalic acid, sulfoisophthalic acid, and ammonium salt, sodium salt, or lower alkyl esterified material of these acids can be used, if necessary. Further, as an acid component, a monobasic acid such as benzoic acid, crotonic acid, or p-tert-butylbenzoic acid can be used in combination in order to adjust a molecular weight or the like.

Examples of the polyhydric alcohol compound include dihydric alcohol such as ethylene glycol, diethylene glycol, propylene glycol, 1,4-butanediol, neopentyl glycol, 3-methylpentanediol, 1,4-hexanediol, and 1,6-hexanediol. In addition, a tri- or higher polyhydric alcohol such as glycerin, trimethylolethane, trimethylolpropane, or pentaerythritol; a polyhydric alcohol including a polyoxyethylene group; or the like can be used in combination therewith, if necessary. These polyhydric alcohols can be used alone or in combination of two or more kinds thereof. In addition, a part of the acid component and the alcohol component can also be substituted with an oxy acid component such as dimethylolpropionic acid, oxypivalic acid, or paraoxybenzoic acid; lower alkyl ester of these acids; or lactones such as ε-caprolactone.

Examples of the oil fatty acid include a coconut oil fatty acid, a soybean oil fatty acid, a linseed oil fatty acid, a safflower oil fatty acid, a tall oil fatty acid, a dehydrated castor oil fatty acid, and a tung oil fatty acid.

In addition, an epoxy-modified alkyd resin prepared by using an epoxy compound for a part of the raw materials, or a vinyl-modified alkyd resin obtained by graft polymerization with a vinyl monomer such as styrene or (meth) acrylic acid ester can also be used. Further, a polyester resin (hereinafter, abbreviated as "recycled PES") produced using, as a main raw material, terephthalic acid recycled from polyethylene terephthalate collected for recycling of resources (for example, PET bottles), polyethylene terephthalate as industrial waste, waste generated in a case of manufacturing polyester products (films, fiber, car components, electronic components, and the like) such as polyethylene terephthalate or polybutylene terephthalate prepared by using terephthalic acid as a main raw material, or the like, can be used. A recycled PES-modified alkyd resin obtained by dissolving this recycled PES in a mixture of the alcohol component and the polybasic acid component, and allowing depolymerization and esterification can be also used.

Examples of the pigment include an inorganic pigment such as a titanium dioxide, an iron oxide, a cadmium sulfide, a calcium carbonate, a barium carbonate, a barium sulfate, clay, talc, chrome yellow, or carbon black; and an organic pigment such as an azo-based organic pigment, a diazo-based organic pigment, a condensed azo-based organic pigment, a thioindigo-based organic pigment, an indanthrone-based organic pigment, a quinacridone-based organic pigment, an anthraquinone-based organic pigment, a benzimidazolone-based organic pigment, a perylene-based organic pigment, a perinone-based organic pigment, a phthalocyanine-based organic pigment, a halogenated phthalocyanine-based organic pigment, an anthrapyridine-based organic pigment, or a dioxazine-based organic pigment. These may be used alone or in combination of two or more kinds thereof. The amount of these pigments mixed depends on the purpose or the desired performance of the coating material, and is normally preferably in a range of 20 to 70 parts by mass in 100 parts by mass of the coating material.

The drying inhibitor is added in order to improve storage stability of the coating material and prevent skinning, and examples thereof include hydroquinone, methoquinone, and tert-butyl hydroquinone. The amount of the drying inhibitor mixed depends on the purpose or the desired performance of the coating material, and is normally in a range of 0.01 to 5 parts by mass in 100 parts by mass of the coating material.

Examples of the organic solvent include "Spindle Oil No. 1", "Solvent No. 3", "Solvent No. 4", "Solvent No. 5", "Solvent No. 6", "Naphtesol H", and "Alkene 56NT" manufactured by JXTG Nippon Oil & Energy Corporation; "Diadol 13" and "Dialen 168" manufactured by Mitsubishi Chemical Corporation; "F OXOCOL" and "F OXOCOL 180" manufactured by NISSAN CHEMICAL INDUSTRIES, Ltd.; "AF Solvent No. 4", "AF Solvent No. 5", "AF Solvent No. 6", And "AF Solvent No. 7" manufactured by JXTG Nippon Oil & Energy Corporation; D-SOL solvent "Solvent H" manufactured by ISU EXACHEM Co., Ltd.; "N-Paraffin C14-C18" manufactured by ISU EXACHEM Co., Ltd.; "Supersol LA35" and "Supersol LA38" manufactured by Idemitsu Kosan Co., Ltd.; "Exxsol D80", "Exxsol D110", "Exxsol D120", "Exxsol D130", "Exxsol D160", "Exxsol D100K", "Exxsol D120K", "Exxsol D130K", "Exxsol D280", "Exxsol D300", and "Exxsol D320" manufactured by EXXON Chemical Co., Ltd.; and "Magiesol 40", "Magiesol 44", "Magiesol 47", "Magiesol 52", and "Magiesol 60" manufactured by Magie Brothers Oil Company, in addition to a hydrocarbon-based solvent such as toluene, xylene, heptane, hexane, or mineral spirit, an alcohol-based solvent such as methanol, ethanol, propanol, or cyclohexanol, a ketone-based solvent such as methyl ethyl ketone, methyl isobutyl ketone, or cyclohexanone, and an ether-based solvent such as propyl ether, methyl cellosolve, cellosolve, butyl cellosolve, or methyl carbitol. The amount of the organic solvent added depends on the purpose or the desired performance of the coating material, and is normally in a range of 20 to 80 parts by mass in 100 parts by mass of the coating material.

Examples of the method for producing the coating material include a method in which a mixture of the oxidative polymerization type unsaturated resin, the pigment, the organic solvent, and various additives is mixed with various mixers such as a paint shaker. The curing accelerator for an oxidative polymerization type unsaturated resin of the present invention may be added at the time of mixing, or may be added after mixing. Further, as the method for adding the curing accelerator for an oxidative polymerization type unsaturated resin, it may be added as a curing accelerator for an oxidative polymerization type unsaturated resin obtained by mixing the compound (A) and the metal salt (B) in advance as described above, or the compound (A) and the metal salt (B) may be separately mixed.

The coating material of the present invention can be applied on a material to be coated, dried and cured by usual methods to obtain a coating film. Here, as a base material (material to be coated) capable of being coated with the coating material of the present invention, steel or the like is used, for example. In addition, as drying conditions (curing conditions) after the coating, room-temperature drying is used. Further, the coating material of the present invention is particularly useful as a coating material for thick coating, because the coating material of the present invention can exhibit excellent curing properties, even in a case of a thick coating film. Specifically, a film thickness of the cured coating film can be in a range of 1 to 500 μm. Accordingly, the coating material of the invention is useful as coating materials for building.

EXAMPLES

Hereinafter, the present invention will be described more specifically with reference to specific examples. In the examples, "part" and "%" are based on mass, unless otherwise noted.

The MS spectrum was measured by using a double focusing mass spectrometer "AX505H (FD505H)" manufactured by JEOL Ltd.

Preparation Example 1: Preparation of Manganese Picolinate

To the flask was added 14.3 g of picolinic acid and 100 g of water, and 23.2 g of a 5M aqueous sodium hydroxide solution and 10.0 g of manganese sulfate were added in this order, and the reaction solution was stirred at 50° C. for 3 hours. The precipitated solid was collected and dried to obtain manganese picolinate. In the MS spectrum of the product, a peak assumed as a peak of a complex in which two picolinic acid ions were coordinated with a manganese (II) ion was confirmed at a mass-to-charge ratio (m/z) of 299.0. The MS spectrum of the product is shown in FIG. 1.

Preparation Example 2: Preparation of Iron Picolinate

To the flask was added 22.8 g of picolinic acid and 100 g of water, and 37.0 g of a 5M aqueous sodium hydroxide solution and 10.0 g of iron (III) chloride were added in this order, and the reaction solution was stirred at 50° C. for 3 hours. The precipitated solid was collected and dried to obtain iron picolinate. In the MS spectrum of the product, a peak assumed as a peak of a complex in which two picolinic acid ions were coordinated with an iron (II) ion was confirmed at a mass-to-charge ratio (m/z) of 300.1.

Examples 1 to 7: Preparation of Curing Accelerator for Oxidation Polymerization Type Unsaturated Resin Components were mixed according to proportions shown in the following Table 1, and curing accelerators for oxidative polymerization type unsaturated resin (1) to (7) were prepared.

Details of each component used in Table 1 are as follows.

Manganese neodecanoate solution: "Mn-NEODECOATE 6.5%" manufactured by DIC Corporation, benzyl alcohol solution having a manganese content of 6.5% by mass Picolinic acid: "Pyridine-2-carboxylic Acid" manufactured by Tokyo Chemical Industry Co., Ltd.

Quinaldic acid: "Quinaldic Acid" manufactured by Tokyo Chemical Industry Co., Ltd.

2,6-Pyridinedicarboxylic acid: "2,6-Pyridindicarboxylic Acid" manufactured by Tokyo Chemical Industry Co., Ltd.

Benzyl alcohol: "Benzyl alcohol (for industrial purposes)" manufactured by Tokyo Ohka Kogyo Co., Ltd.

1-Methylimidazole: "1-Methylimidazole" manufactured by Tokyo Chemical Industry Co., Ltd.

TABLE 1

| Curing accelerator for oxidative polymerization type unsaturated resin | (1) | (2) | (3) | (4) | (5) | (6) | (7) |
|---|---|---|---|---|---|---|---|
| Manganese neodecanoate benzyl alcohol solution [parts by mass] | 10 | 10 | 10 | 10 | 10 | | |
| Picolinic acid [parts by mass] | 1.5 | | | | 1.5 | | |
| Quinaldic acid [parts by mass] | | 2.1 | | | | | |
| Methyl picolinate [parts by mass] | | | 1.6 | | | | |
| 2,6-pyridinedicarboxylic acid [parts by mass] | | | | 2.0 | | | |
| Manganese picolinate obtained by Preparation Example 1 [parts by mass] | | | | | | 10 | |
| Iron picolinate obtained by Preparation Example 2 [parts by mass] | | | | | | | 10 |
| Benzyl alcohol [parts by mass] | 43 | 42 | 43 | 42 | | | |
| 1-Methylimidazole [parts by mass] | | | | | 43 | 137 | 118 |

Examples 8 to 14 and Comparative Examples 1 to 3: Preparation and Evaluation of Coating Materials Each component was mixed according to proportions shown in the following Table 2, and coating materials (1) to (7), (1') to (3') were prepared. The resulting coating materials were evaluated for curing properties in the following manner. The results are shown in Table 2. The base coating material was prepared in the following manner.

Details of each component used in Table 2 are as follows.

Anti-skinning agent: "Methyl ethyl ketoxime" manufactured by Ube Industries, Ltd.

Manganese neodecanoate soap: "DICNATE Mn 6.5%" manufactured by DIC Corporation, soybean oil solution having a manganese content of 6.5% by mass Cobalt octylate soap: "DICNATE210SB" manufactured by DIC Corporation, soybean oil solution having a cobalt content of 10% by mass Zirconium soap: "12% Zr-OCTOATE" manufactured by DIC Corporation, mineral spirit solution having a zirconium content of 12% by mass Preparation Example 3: Preparation of Base Coating Material 100 parts by mass of Titanium white pigment ("Ti-Pure R-960" manufactured by Chemours Co., Ltd.), 40 parts by mass of calcium carbonate ("NS #100" manufactured by Nitto Funka Kogyo K.K.), 240 parts by mass of alkyd resin ("Alukidir P-470-70" manufactured by DIC Corporation) and 20 parts by mass of mineral spirit ("Mineral Spirit A" manufactured by JXTG Nippon Oil & Energy Co., Ltd.) were kneaded with a paint shaker to obtain a base coating material.

Evaluation of Curing Properties of Coating Materials

The test was carried out in a constant temperature and humidity chamber (23±2° C., 50±5% RH). The previously obtained coating material was applied to a glass plate with an applicator of 76 μm. After the application, the time until the coating material was completely dried and a scratch applied by a needle of a drying time recorder ("Model No. 404" manufactured by Taiyu Kizai Co., Ltd.) was not observed was measured.

Examples 15 to 18: Preparation and Evaluation of Printing Inks

Components were mixed according to proportions shown in the following Table 3, and printing inks (1) to (4) were prepared. The resulting printing inks were evaluated for curing properties in the following manner. The results are shown in Table 3. The base ink was prepared in the following manner.

Preparation Example 4: Preparation of Base Ink 100 parts by mass of a rosin-modified phenolic resin ("BECKACITE F-7310" manufactured by DIC Corporation) and 100 parts by mass of soybean oil ("Soybean Salad Oil (S)" manufactured by The Nisshin Oillio Group, Ltd.) were heated at 210° C. for 1 hour, and 47.5 parts by mass of an organic solvent ("AF Solvent No. 6" manufactured by JXTG Nippon Oil & Energy Co., Ltd.) and 2.5 parts by mass of an aluminum chelate ("Chelope (S)" manufactured by Hope Chemical Co., Ltd.) were added thereto, and the mixture was heated at 150° C. for 1 hour to prepare a varnish for printing ink.

100 parts by mass of the previously obtained varnish for printing ink, 20 parts by mass of a phthalocyanine blue pigment ("FASTOGEN BLUE TGR-L" manufactured by DIC Corporation), 25 parts by mass of soybean oil ("Soybean Salad Oil (S)" manufactured by The Nisshin Oillio Group, Ltd.), and 25 parts by mass of an organic solvent ("AF Solvent No. 6" manufactured by JXTG Nippon Oil & Energy Co., Ltd.) were kneaded in a three-roll mill to obtain a base ink.

Evaluation of Curing Properties of Printing Ink

The test was carried out in a constant temperature and humidity chamber (23±2° C., 50±5% RH). The previously obtained printing ink was applied to a glass plate with an applicator of 38 μm. After the application, the time until the ink was completely dried and a scratch applied by a needle of a drying time recorder ("Model No. 404" manufactured by Taiyu Kizai Co., Ltd.) was not observed was measured.

TABLE 2

|  |  | Example 8 | Example 9 | Example 10 | Example 11 | Example 12 | Example 13 | Example 14 | Comparative Example 1 | Comparative Example 2 | Comparative Example 3 |
|---|---|---|---|---|---|---|---|---|---|---|---|
| Coating Material |  | (1) | (2) | (3) | (4) | (5) | (6) | (7) | (1') | (2') | (3') |
| Base coating material [parts by mass] |  | 100 | 100 | 100 | 100 | 100 | 100 | 100 | 100 | 100 | 100 |
| Anti-skinning agent [parts by mass] |  | 0.2 | 0.2 | 0.2 | 0.2 | 0.2 | 0.2 | 0.2 | 0.2 | 0.2 | 0.2 |
| Curing accelerator for oxidative polymerization type unsaturated resin [parts by mass] | (1) | 0.5 |  |  |  |  |  |  |  |  |  |
|  | (2) |  | 0.5 |  |  |  |  |  |  |  |  |
|  | (3) |  |  | 0.5 |  |  |  |  |  |  |  |
|  | (4) |  |  |  | 0.5 |  |  |  |  |  |  |
|  | (5) |  |  |  |  | 0.5 |  |  |  |  |  |
|  | (6) |  |  |  |  |  | 0.5 |  |  |  |  |
|  | (7) |  |  |  |  |  |  | 0.5 |  |  |  |
| Manganese neodecanoate soap [parts by mass] |  |  |  |  |  |  |  |  | 0.1 |  |  |
| Cobalt octylate soap [parts by mass] |  |  |  |  |  |  |  |  |  | 0.25 | 0.05 |
| Zirconium soap [parts by mass] |  | 0.6 | 0.6 | 0.6 | 0.6 | 0.6 | 0.6 | 0.6 | 0.6 | 0.6 | 0.6 |
| Metal content in Coating material [% by mass] | Manganese | 0.006 | 0.006 | 0.006 | 0.006 | 0.006 | 0.006 | — | 0.006 | — | — |
|  | Iron |  |  |  |  |  | 0.006 |  | — | — | — |
|  | Cobalt | — | — | — | — | — | — | — | — | 0.025 | 0.005 |
| Drying time [hour] |  | 9.2 | 8.6 | 8.8 | 7.2 | 4.9 | 4.2 | 8.8 | 15.3 | 9.4 | 10.3 |

TABLE 3

|  |  | Example 15 | Example 16 | Example 17 | Example 18 |
|---|---|---|---|---|---|
| Printing ink |  | (1) | (2) | (3) | (4) |
| Base ink [parts by mass] |  | 100 | 100 | 100 | 100 |
| Curing accelerator for oxidative polymerization type unsaturated resin [parts by mass] | (1) | 2 |  |  |  |
|  | (6) |  | 1 | 2 |  |
|  | (7) |  |  |  | 2 |
| Metal content [% by mass] | Manganese | 0.024 | 0.012 | 0.020 |  |
|  | Iron | — | — | — | 0.020 |
| Drying time [hour] |  | 16.9 | 15.7 | 14.2 | 17.3 |

The invention claimed is:

1. A curing accelerator for an oxidative polymerization type unsaturated resin, comprising:
a metal complex (β) having manganese or iron as a central metal and having an anion compound (a) represented by the following structural formula (1-1) or (1-2) as a ligand:

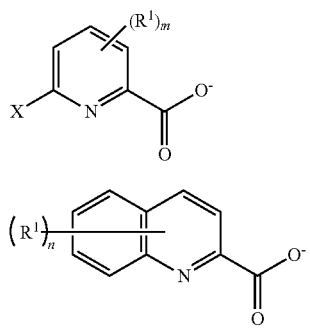

wherein $R^1$ is any one of a hydroxyl group, an amino group, a nitro group, a nitroso group, a sulfo group, a halogen atom, a hydrocarbon group which may have a substituent, a hydrocarbon oxy group which may have a substituent, and a hydrocarbon oxycarbonyl group which may have a substituent, m is 0 or an integer of 1 to 3, n is 0 or an integer of 1 to 6, and X is any one of a carboxylate group, a hydrogen atom, and a $R^1$ group;
at least one of an imidazole compound (C); and
a benzyl alcohol compound (D).

2. A curable resin composition comprising an oxidative polymerization type unsaturated resin and a curing accelerator for an oxidative polymerization type unsaturated resin, comprising a metal complex (β) having manganese or iron as a central metal and having an anion compound (α) represented by the following structural formula (1-1) or (1-2) as a ligand:

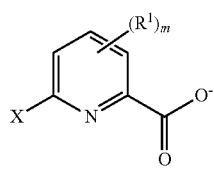

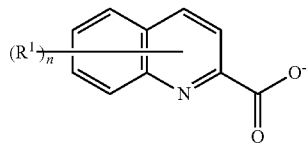

wherein $R^1$ is any one of a hydroxyl group, an amino group, a nitro group, a nitroso group, a sulfo group, a halogen atom, a hydrocarbon group which may have a substituent, a hydrocarbon oxy group which may have a substituent, and a hydrocarbon oxycarbonyl group which may have a substituent, m is 0 or an integer of 1 to 3, n is 0 or an integer of 1 to 6, and X is any one of a carboxylate group, a hydrogen atom, and a $R^1$ group.

3. The curable resin composition according to claim 2, which is a printing ink or a coating material.

4. A method for preparing a curable resin composition of claim 2, comprising mixing a compound (A) represented by the following structural formula (2-1) or (2-2):

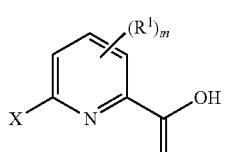

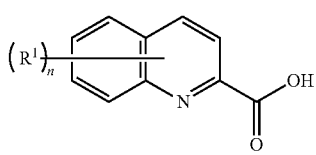

wherein $R^1$ is any one of a hydroxyl group, an amino group, a nitro group, a nitroso group, a sulfo group, a halogen atom, a hydrocarbon group which may have a substituent, a hydrocarbon oxy group which may have a substituent, and a hydrocarbon oxycarbonyl group which may have a substituent, m is 0 or an integer of 1 to 3, n is 0 or an integer of 1 to 6, and X is any one of a carboxy group, a hydrogen atom, and a $R^1$ group; a metal salt (B) of manganese or iron; and an oxidative polymerization type unsaturated resin.

5. A curing accelerator for an oxidative polymerization type unsaturated resin, comprising:
a metal complex (β2) having an anion compound (α) represented by the following structural formula (1-1) or (1-2) as a ligand:

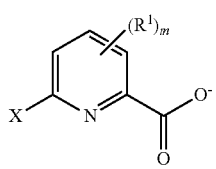

-continued

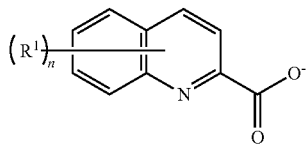 (1-2)

wherein R¹ is any one of a hydroxyl group, an amino group, a nitro group, a nitroso group, a sulfo group, a halogen atom, a hydrocarbon group which may have a substituent, a hydrocarbon oxy group which may have a substituent, and a hydrocarbon oxycarbonyl group which may have a substituent, m is 0 or an integer of 1 to 3, n is 0 or an integer of 1 to 6, and X is any one of a carboxylate group, a hydrogen atom, and a R¹ group, wherein the metal complex (β2) comprises a metal salt represented by the following general formula (B-1):

M(X)ₙ         (B-1)

wherein M is manganese or iron as a central metal, X is any one of $F^-$, $Cl^-$, $Br^-$, $I^-$, $PF_6^-$, $SbF_6^-$, $AsF_6^-$, $BF_4^-$, $B(C_6F_5)_4^-$, $ClO_4^-$, $ClO_3^-$, $CO_2^-$, $ClO^-$, $H_2PO_4^-$, $H_2PO_3^-$, $H_2PO_2^-$, $HCO_3^-$, $NO_3^-$, $NO_2^-$, $(CH_3CO)_2CH^-$, $RCOO^-$ (wherein R is a hydrocarbon group having 1 to 22 carbon atoms), $O^{2-}$, $S^{2-}$, $SO_4^{2-}$, $SO_3^{2-}$, and $CO_3^{2-}$; and n is an integer of 1 or more;
at least one of an imidazole compound (C); and
a benzyl alcohol compound (D).

6. A curable resin composition comprising an oxidative polymerization type unsaturated resin and a curing accelerator for an oxidative polymerization type unsaturated resin, comprising a metal complex (β2) having an anion compound (α) represented by the following structural formula (1-1) or (1-2) as a ligand:

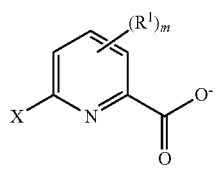 (1-1)

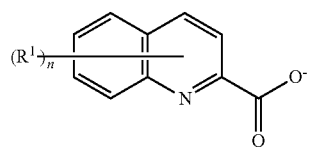 (1-2)

wherein R¹ is any one of a hydroxyl group, an amino group, a nitro group, a nitroso group, a sulfo group, a halogen atom, a hydrocarbon group which may have a substituent, a hydrocarbon oxy group which may have a substituent, and a hydrocarbon oxycarbonyl group which may have a substituent, m is 0 or an integer of 1 to 3, n is 0 or an integer of 1 to 6, and X is any one of a carboxylate group, a hydrogen atom, and a R¹ group, wherein the metal complex (β2) comprises a metal salt represented by the following general formula (B-1):

M(X)ₙ         (B-1)

wherein M is manganese or iron as a central metal, X is any one of $F^-$, $Cl^-$, $Br^-$, $I^-$, $PF_6^-$, $SbF_6^-$, $AsF_6^-$, $BF_4^-$, $B(C_6F_5)_4^-$, $ClO_4^-$, $ClO_3^-$, $CO_2^-$, $ClO^-$, $H_2PO_4^-$, $H_2PO_3^-$, $H_2PO_2^-$, $HCO_3^-$, $NO_3^-$, $NO_2^-$, $(CH_3CO)_2CH^-$, $RCOO^-$ (wherein R is a hydrocarbon group having 1 to 22 carbon atoms), $O^{2-}$, $S^{2-}$, $SO_4^{2-}$, $SO_3^{2-}$, and $CO_3^{2-}$; and n is an integer of 1 or more.

7. The curable resin composition according to claim 6, which is a printing ink or a coating material.

8. A method for preparing a curable resin composition of claim 6, comprising mixing a compound (A) represented by the following structural formula (2-1) or (2-2):

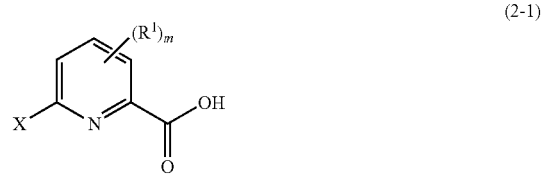 (2-1)

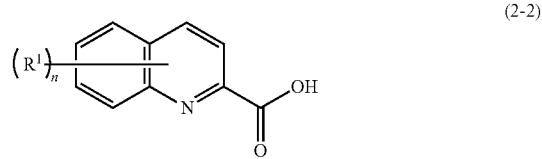 (2-2)

wherein R¹ is any one of a hydroxyl group, an amino group, a nitro group, a nitroso group, a sulfo group, a halogen atom, a hydrocarbon group which may have a substituent, a hydrocarbon oxy group which may have a substituent, and a hydrocarbon oxycarbonyl group which may have a substituent, m is 0 or an integer of 1 to 3, n is 0 or an integer of 1 to 6, and X is any one of a carboxy group, a hydrogen atom, and a R¹ group; a metal salt (B) of manganese or iron; and an oxidative polymerization type unsaturated resin.

9. A curable resin composition comprising:
a curing accelerator for an oxidative polymerization type unsaturated resin, comprising a compound (A) represented by the following structural formula (2-1) or (2-2):

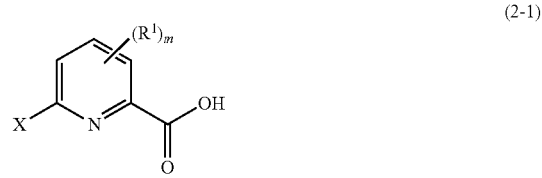 (2-1)

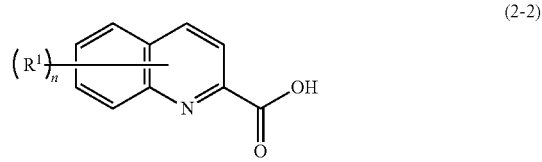 (2-2)

wherein R¹ is any one of a hydroxyl group, an amino group, a nitro group, a nitroso group, a sulfo group, a halogen atom, a hydrocarbon group which may have a substituent, a hydrocarbon oxy group which may have a substituent, and a hydrocarbon oxycarbonyl group which may have a substituent, m is 0 or an integer of 1 to 3, n is 0 or an integer of 1 to 6, R² is a hydrogen atom or an aliphatic hydrocarbon group, and X is any one of —COOR$^2$ group, a hydrogen atom, and a R$^1$ group, and a metal salt (B) comprising a manganese salt or an iron salt as an essential component; and at least one oxidative polymerization type unsaturated resin selected from a rosin-modified phenolic resin, an alkyd resin, a petroleum resin, polymerized oil, an unsaturated group-containing urethane resin, and an unsaturated group-containing epoxy resin.

10. The curable resin composition according to claim 9, which is a printing ink or a coating material.

* * * * *